United States Patent
Hewitt et al.

(10) Patent No.: US 7,507,229 B2
(45) Date of Patent: Mar. 24, 2009

(54) WIRE BRAID-REINFORCED MICROCATHETER

(75) Inventors: Todd J. Hewitt, Laguna Niguel, CA (US); Michael D. Martel, Orange, CA (US); Peter Davis, Dana Point, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 255 days.

(21) Appl. No.: 10/683,877

(22) Filed: Oct. 10, 2003

(65) Prior Publication Data

US 2004/0153049 A1 Aug. 5, 2004

Related U.S. Application Data

(60) Provisional application No. 60/417,182, filed on Oct. 10, 2002.

(51) Int. Cl.
*A61M 25/00* (2006.01)
(52) U.S. Cl. ....................... 604/527; 604/525
(58) Field of Classification Search ................ 604/527, 604/525; 606/194
See application file for complete search history.

(56) References Cited

U.S. PATENT DOCUMENTS

| | | | |
|---|---|---|---|
| 5,154,795 A | 10/1992 | Ishida et al. | |
| 5,533,987 A * | 7/1996 | Pray et al. | 604/527 |
| 5,662,622 A * | 9/1997 | Gore et al. | 604/526 |
| 5,676,659 A * | 10/1997 | McGurk | 604/527 |
| 5,695,480 A * | 12/1997 | Evans et al. | 604/264 |
| 5,702,373 A | 12/1997 | Samson | |
| 5,704,926 A | 1/1998 | Sutton | |
| 5,713,867 A | 2/1998 | Morris | |
| 5,860,963 A * | 1/1999 | Azam et al. | 604/528 |
| 5,951,539 A | 9/1999 | Nita et al. | |
| 6,042,578 A | 3/2000 | Dinh et al. | |
| 6,053,904 A * | 4/2000 | Scribner et al. | 604/527 |
| 6,143,013 A | 11/2000 | Samson et al. | |
| 6,186,978 B1 * | 2/2001 | Samson et al. | 604/96.01 |
| 6,213,995 B1 | 4/2001 | Steen et al. | |
| 6,531,111 B1 | 3/2003 | Whalen et al. | |
| 6,841,214 B1 * | 1/2005 | Keith et al. | 428/35.8 |
| 2002/0090339 A1 * | 7/2002 | Whalen et al. | 424/9.4 |
| 2004/0153049 A1 | 8/2004 | Hewitt et al. | |

FOREIGN PATENT DOCUMENTS

| EP | 0 594 201 | 4/1994 |
|---|---|---|
| WO | 96/33763 | 10/1996 |

* cited by examiner

*Primary Examiner*—Nicholas D Lucchesi
*Assistant Examiner*—Laura A Bouchelle
(74) *Attorney, Agent, or Firm*—Foley & Lardner LLP

(57) ABSTRACT

This invention is directed to a multi-layer catheter for navigation to remote locations within the body, comprising a liner layer, a braid layer and an outer jacket. The catheter provides a high degree of flexibility needed to traverse the vasculature and a high degree of strength needed to withstand the high pressures associated with catheter-delivery of viscous embolizing compositions.

18 Claims, 5 Drawing Sheets

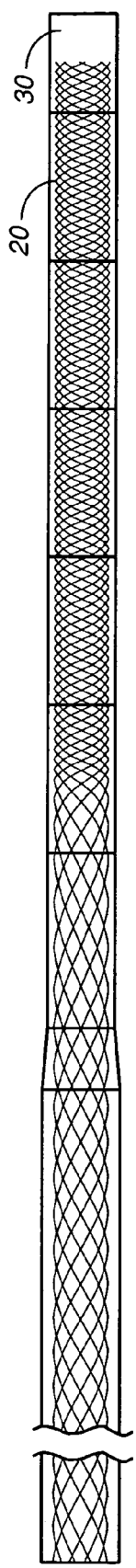
FIG._1
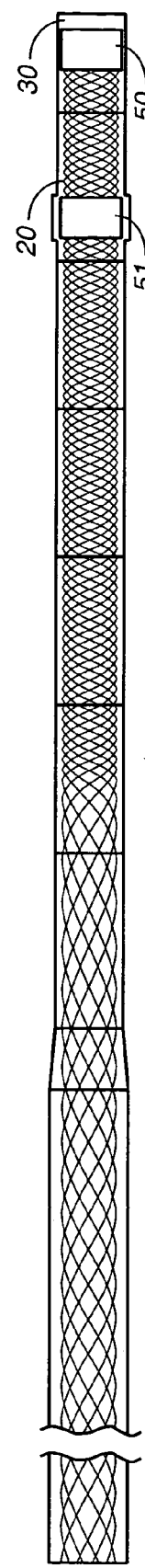
FIG._2
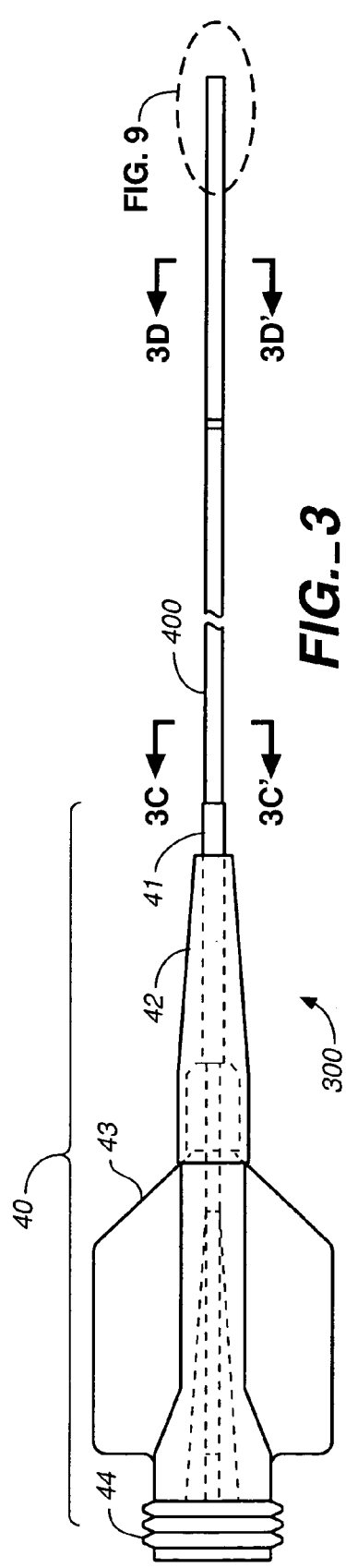
FIG._3
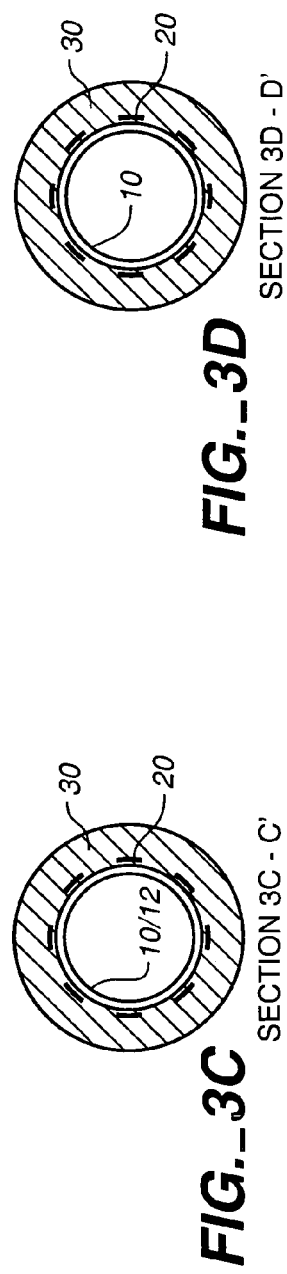
FIG._3D  SECTION 3D - D'
FIG._3C  SECTION 3C - C'

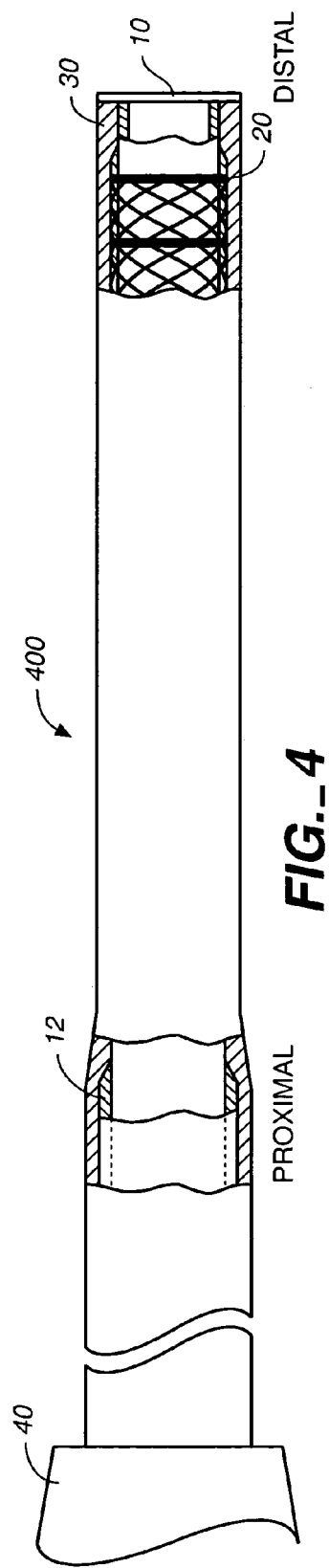
FIG._4
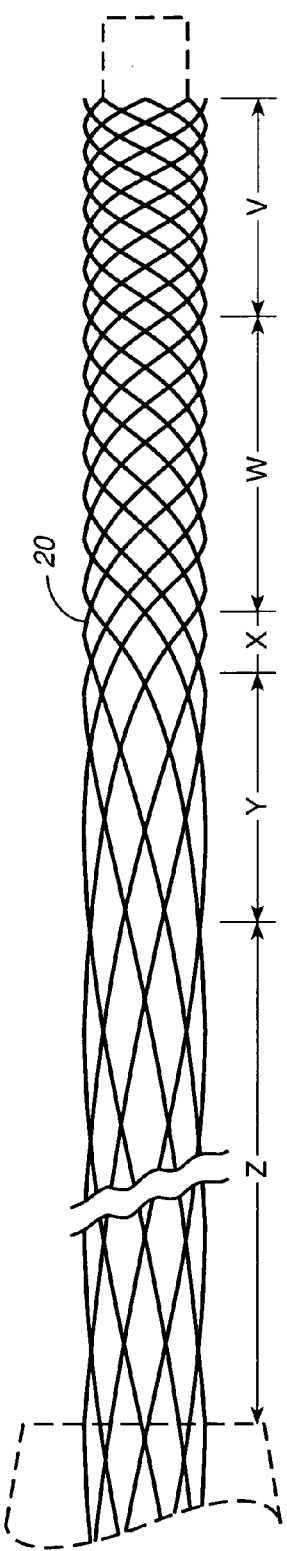
FIG._6
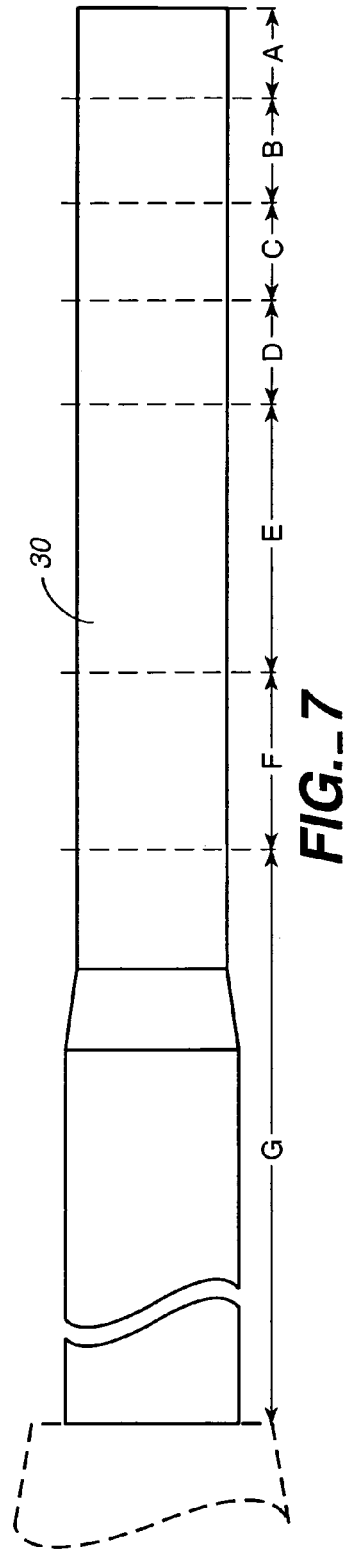
FIG._7

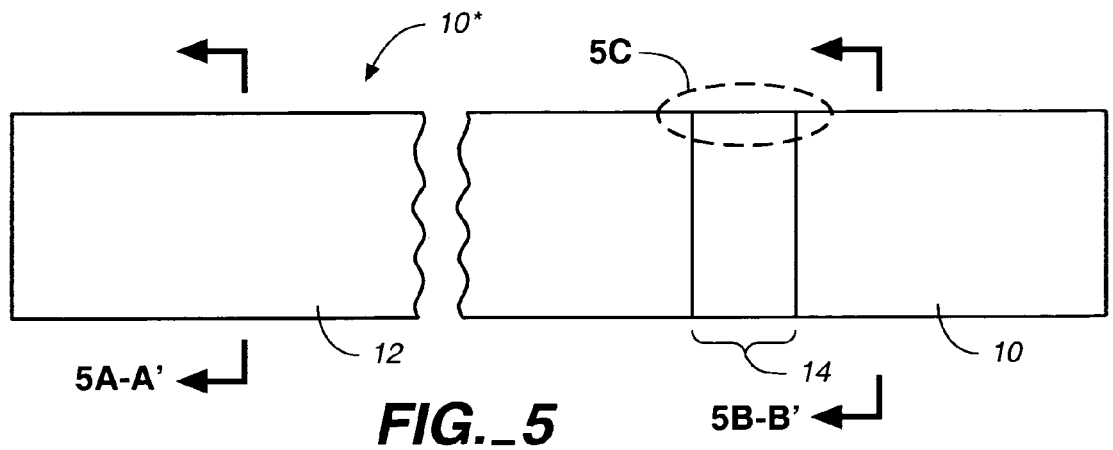
FIG._5
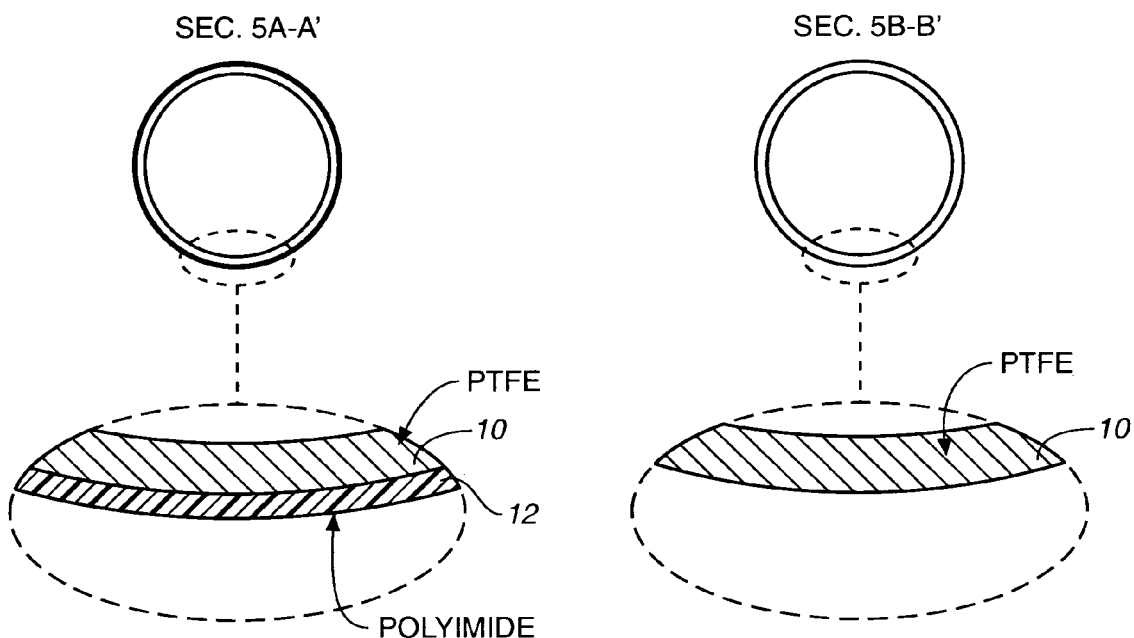
FIG._5A  FIG._5B
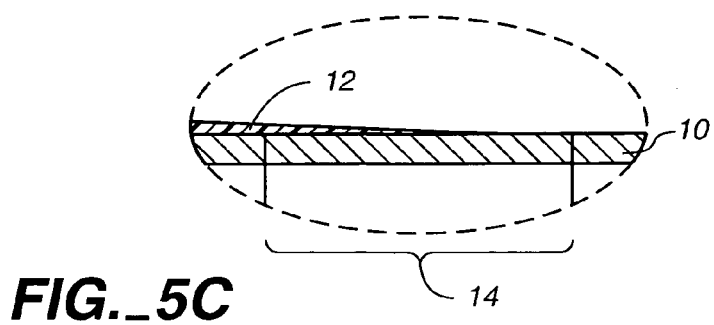
FIG._5C

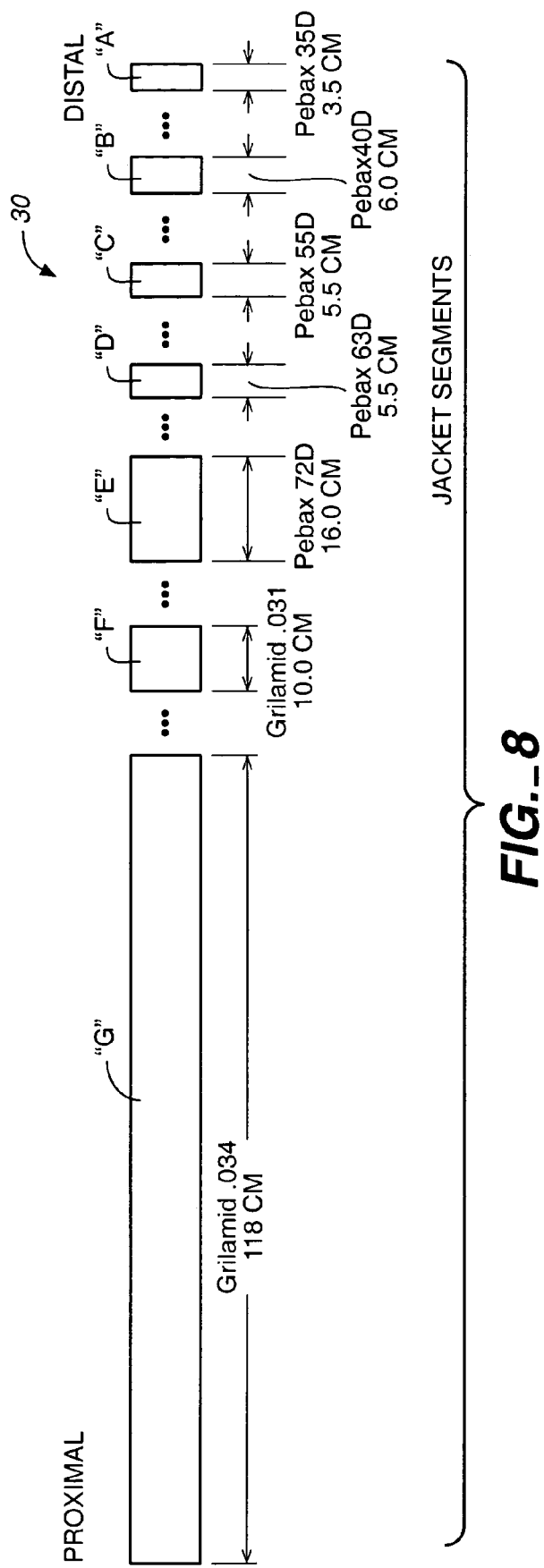
FIG._8

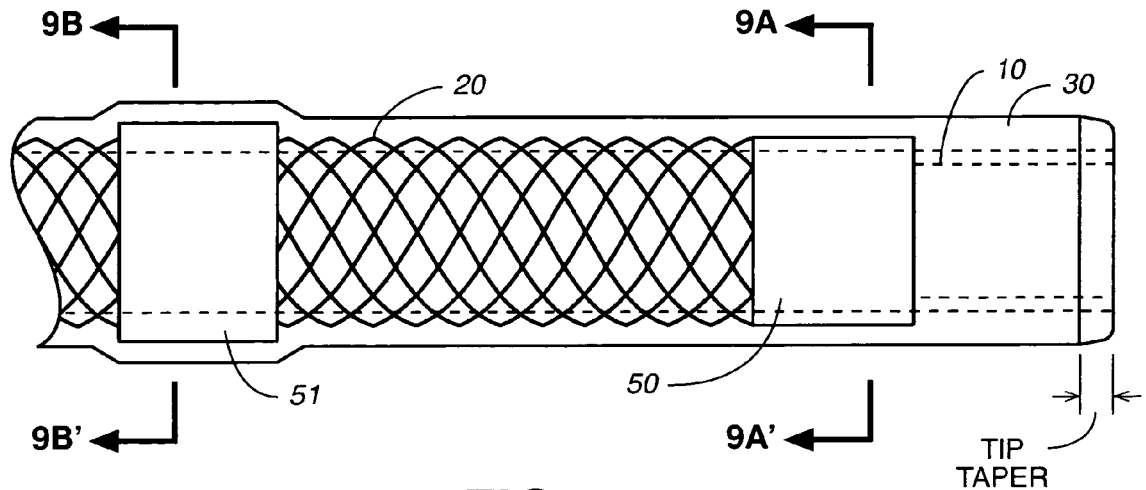
FIG._9
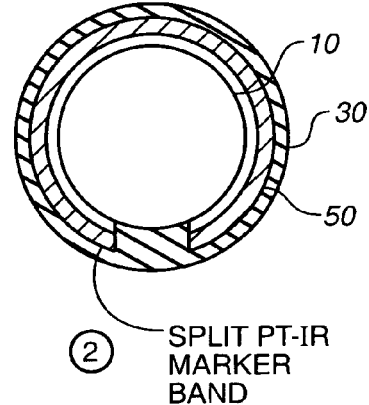
SECTION 9A-9A'
FIG._9A
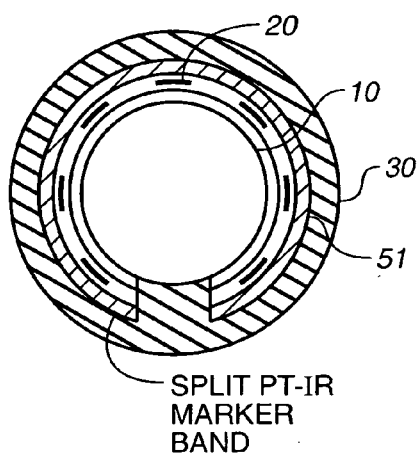
SECTION 9B-9B'
FIG._9B

WIRE BRAID-REINFORCED MICROCATHETER

REFERENCE TO RELATED APPLICATION

The application claims the benefit of U.S. Provisional Patent Application Ser. No. 60/417,182, filed on Oct. 10, 2002.

FIELD OF THE INVENTION

The invention relates to wire-reinforced catheters for navigation to remote locations within the body of a patient.

DESCRIPTION OF THE RELATED ART

Wire-reinforced catheters are well known in the art. Generally, these consist of an elongated, flexible tubular body defining a central lumen extending from one end of the body to the other end. A distal end of the catheter is delivered into the body of a patient and located at a treatment site. The proximal end of the catheter remains outside of the patient's body for manipulation by the treating physician. The lumen provides a conduit for delivery of material to or from the body, or for transfer of sensor information from within the interior of the body.

Catheters vary in size from large diameter catheters for use in the urinary tract and in large coronary arteries and the like to much smaller catheters often referred to as "microcatheters" designed and sized to pass through a variety of body conduits and orifices involving small veins and arteries.

The materials delivered through catheters also vary, as well, and can range from low viscosity aqueous solutions to more viscous oils, suspensions and the like. Wire coils and filaments can also be delivered through catheters to various body sites.

One application of special interest involves delivering high viscosity embolizing compositions through catheters. U.S. Pat. No. 6,531,111, issued Mar. 11, 2003, to Whalen, et al., and incorporated herein by reference, describes compositions for embolizing blood vessels which are particularly suited for treating vascular lesions via catheter delivery. These compositions include a biocompatible polymer, a contrast agent and a biocompatible solvent, and have a viscosity of at least 150 cSt at 40° C. and preferably have a viscosity of a least 200 and especially at least 500 cSt at this same temperature. These viscous embolic compositions are attractive because of their much-reduced unintended migration during use.

This sort of viscous embolizing composition finds use in stabilizing and correcting aneurysms in complex body environments such as the brain. In these cases it is generally required to deliver the compositions through long catheters (such as 100-200 cm long) which pass through complex small diameter vessels and arteries. This calls for microcatheters generally having an outside diameter of 0.040 inch (0.1 cm) or less and an inner diameter of about 0.030 inches (0.075 cm) or less in order to fit through the small vessels. The catheters must also be quite flexible, particularly at the distal ends which must traverse tight twists and turns in use.

The high viscosity of the embolizing material poses a problem. Forcing a high viscous material through a small diameter of a long microcatheter requires a high injection pressure, at times as much as 300 psi and even up to 700-1000 psi. Such a pressure may exceed the burst pressure of nearly all conventional microcatheters.

It is an object of this invention to provide a microcatheter which is of a size and flexibility so as to traverse small complicated vessel paths while being strong enough to withstand strenuous manipulation and high pressures such as are encountered delivering viscous embolizing compositions.

It is a further object of this invention to provide, in combination, a kit of parts which includes a microcatheter of the type just described in combination with an embolizing composition having a viscosity of at least about 150 cSt and means for driving the composition through the catheter.

STATEMENT OF THE INVENTION

We have now discovered a construction for microcatheters which provides the high degree of flexibility needed to traverse complicated small vessel pathways and the high degree of strength needed to withstand strenuous manipulation and the high pressures associated with catheter-delivery of viscous embolizing compositions.

Structurally, the tubular body of the catheter is formed of a polymeric material, typically formed in multiple layers. One arrangement, of particular interest here, provides a structure in which an inner polymer layer is surrounded by a wound or braided reinforcing wire. Atop this reinforcing wire is overlaid an outer layer or jacket made up of a plurality of joined segments of polymers of increasing flexibility moving proximal to distal, such that the reinforcing wire is sandwiched between the inner and outer layers.

In the catheters of this invention all three of these components, that is the liner, the wire braid, and the outer jacket, are graduated in flexibility being more flexible at their distal ends than at their proximal ends.

BRIEF DESCRIPTION OF THE DRAWING FIGURES

The invention will be described in greater detail with reference to the preferred embodiments illustrated in the accompanying drawings, in which like elements bear like reference numerals, and wherein:

FIG. 1 is a schematic, not to scale side view of one embodiment of a catheter according to the present invention.

FIG. 2 is a schematic, not to scale side view of an embodiment of the catheter of FIG. 1 with marker bands.

FIG. 3 is a partially cross-sectional, not to scale side view of a catheter shown with a representative hub assembly.

FIGS. 3C and 3D are sectional views of the catheter of FIG. 3 taken at various locations along its length.

FIG. 4 is a schematic, not to scale partially cross-sectional view of a catheter of the invention showing the relationships among the inner liner, the metallic braid and the polymer outer jacket and showing the attachment of the catheter lumen to a hub.

FIG. 5 is a schematic, not to scale side view of the inner liner.

FIG. 5A is a section taken at A-A' of the liner of FIG. 5 showing a polyimide stiffening overliner present only on the proximal end of the liner.

FIG. 5B is a section taken at B-B', Distal to A-A' showing the liner without overliner.

FIG. 5C is an axial cross section showing the taper in the overlayer at its distal end.

FIG. 6 is a schematic, not to scale side view of a metal braid illustrating the stepwise increase in pic (weave density) and thus flexibility moving from its proximal to its distal end.

FIG. 7 is a schematic, not to scale side view of the polymer jacket illustrating the various sections of polymer which make it up with the flexibility of the polymer sections increasing moving from the jacket's proximal to distal ends.

FIG. 8 is a schematic, not to scale side view of the cylindrical polymeric sections that are fused together to make a representative outer jacket.

FIG. 9 is a schematic, not to scale partially cross-sectional side view of the tip of a catheter of the invention.

FIGS. 9A and 9B are radial cross-sections taken at A-A' and B-B' showing radiographic marker bands optionally present near the tip of the catheter.

DETAILED DESCRIPTION OF THE INVENTION

As shown in FIG. 4, a catheter 400 of the present invention includes three layers including a liner 10, a braid 20, and an outer jacket 30 assembled to provide varying flexibility along a length of the catheter. The catheter is suitable for accessing a tissue target within the body, typically a target which is accessible through the vascular system. The catheter has improved torque translation, improved proximal shaft column strength and improved distal flexibility over currently available catheters. In addition, the catheter has high burst and tensile strengths to permit delivery of viscous fluids such as these described in U.S. Pat. No. 6,531,111 entitled "High Viscosity Embolizing Compositions," issued Mar. 1, 2003.

As shown in FIGS. 3 and 4, the catheter lumen can be affixed to a hub 40. Typically hub 40 will include strain relief sections 41 and 42, manipulating wings 43 to assist in attaching the catheter to a syringe or other drive unit and a threaded or locking fitting 44 for making the attachment to the syringe or the like.

The three principal components of the catheter lumen itself, that is the inner liner 10 or lubricous liner, the braid 20, and the outer jacket 30 are each described in separate sections hereinbelow.

Preferably, the catheter is a microcatheter. Microcatheters typically have lumen diameters of about 0.008 inches to about 0.03 inches, and more commonly 0.01 to 0.02 inches.

Lubricous Liner

The inner liner of the catheter is a lubricous liner 10 which additionally is configured to provide strengthening and stiffening to the proximal portion of the catheter. The liner 10 prevents the braid 20 from being exposed on the inner surface of the catheter and improves the lubricity of the catheter inner lumen to aid guidewire placement. The liner 10 is formed with a low friction polymer which can be a fluorocarbon such as polytetrafluoroethylene (PTFE), high density polyethylene, other low friction polymers, or combinations thereof. The low friction polymer, such as PTFE, may be combined with an overlayer 12 of another more rigid polymer, such as polyimide to increase the strength of the liner.

When the liner includes a more rigid polymer overlayer 12, such as a layer of polyimide, the wall thickness of the rigid polymer layer gradually tapers or otherwise diminishes in thickness down to zero or essentially zero well before the distal tip. This is shown in FIG. 4 and also in more detail in FIG. 5. In FIG. 5, a liner 10* is shown. It consists of a lubricous tube 10 of, for example PTFE coated on its proximal end with a layer 12 of polyimide. At location 14 the polyimide tapers to zero as shown in FIG. 5C. FIG. 5A shows the inner liner region coated with polyimide. FIG. 5B shows the liner region not coated with polyimide or other strengthening material.

This creates an inner liner having greater strength and reduced flexibility at the proximal end and greater flexibility and reduced strength at the distal end.

Alternatively, but less preferably, the polyimide may be incorporated in the PTFE layer with decreasing concentration toward the distal tip. The distal at least 3-5 cm (and often a much greater proportion of the catheter) preferably is provided with no polyimide or other strengthening polymer for improved distal tip flexibility. This liner design combining a lubricious material and a strengthening material provides for additional burst strength for substantially the length of the catheter with the exception of the distal portion and provides lubricity throughout. In the liner including PTFE or other lubricious material and polyimide or other strengthening material, the PTFE is a radially inward layer of the liner and the polyimide is in a radially outward layer of the liner.

Braided Wire Reinforcement

Surrounding the liner 10 is a layer of braided reinforcement material 20 which is disposed over and conforms to the inner liner 10. The braid material 20 may be formed of a metallic thread, such as Nitinol, stainless steel, or other metal having a cross section which is elliptical, circular, rectangular, ribbon, or other shape. The winding pitch of the reinforcing wire should be varied along the length of the catheter to achieve a desired flexibility profile. As shown in FIGS. 1 and 6, the braid 10 has a variable winding pitch or pic rate. For example, the braid may be formed in three or more sections of differing pic rates. The catheter is provided with a braid having a lower pic rate at the proximal end to provide increased strength and a higher pic rate at the distal end to provide increased kink resistance and flexibility. For example, the proximal end pic rate is preferably less than or equal to 80 pics-per-inch (ppi) and the distal end pic rate is preferably greater than 80 ppi.

In FIG. 6, a representative five section braid is shown with the sections being as follows:

| Section | Pic | Length |
|---|---|---|
| V | 120 | 15 cm |
| W | 80 | 15 cm |
| X | 50 | 5 cm |
| Y | 30 | 15 cm |
| Z | 25 | to proximal end |

This is merely representative although this is the pic pattern used in Examples 2-4, herein with the weave made of elliptical Nitinol wire (0.001"×0.003" or 0.0007"×0.003"). In any event, the pic rate increases moving proximal to distal along the reinforcing braid.

One or more wires can be used, spirally wound in the same or opposite directions. Multiple, counter-woven strands as shown can be considered to form a reinforcing wire mesh or braid between the inner and outer layers of the catheter.

The braid may comprise a superelastic or pseudoelastic material, such as Nitinol. The superelastic or pseudoelastic material can be annealed prior to assembly of the catheter to provide a desired strength or flexibility or even a varying flexibility along the catheter length. The braid may be formed by weaving the superelastic or pseudoelastic wire over a mandrel and then annealing. Varying flexibility can be further achieved by variable annealing of separate pieces of braid or by variable annealing of the different sections of a continuous braid. Annealing at a higher temperature and/or for a longer period of time at the distal end of the braid will produce a softer distal section. The combination of high pic rate and increased annealing at the distal end can produce a braid which is more flexible than the braid with a high pic rate alone.

Preferably, the braided-reinforcement spans the entire length of the catheter from the proximal end to near, that is to within about 10 cm to about 1 cm of the distal tip. The braided-reinforcement may be formed as one braid spanning the entire catheter or may be formed of multiple segments which may each include a single or variable pic rate. When two or more braids are used, the braids may be overlapped, welded, or otherwise fixed to each other to facilitate increased tensile strength and kink resistance. Alternatively, the proximal end of the reinforcement may be formed as a coil rather than a braid.

According to another embodiment, the braid can be formed of wires of two or more materials. For example, a portion of the wires in the braid may be stainless steel and the other portion of the wires may be Nitinol. The stainless steel providing increased pushability and the Nitinol providing shape memory. Further, the braid can be formed of wires having one or more different cross sections. For example, half of the wires in the braid may be circular while the other half of the wires are rectangular. The wires can have a largest cross sectional dimension of about 0.015 inches to about 0.0005 inches, preferably about 0.005 inches to about 0.001 inches.

Outer Jacket

As shown in FIG. 7, the outer jacket 30 includes at least two and preferably 5-10 segments shown as "A", "B", "C" . . . in FIG. 7. These sections vary in durometer of their polymers, wherein the proximal durometers are higher than the more distal durometers. The outer jacket can be formed of segments of one or more polymers, such as Grilamid brand polyamide/nylon from EMS Chemie, Switzerland, Pebax brand polyether/polyamide, from Actinofina Chemicals, France and the like.

The outer jacket is prepared by obtaining segments of desired lengths of cylindrical stock of the various polymers and joining these segments typically by heat fusing. The proximal segment is typically quite long relative to the others and is the most rigid and strongest segment. In FIGS. 7 and 8, where a 7 segment jacket is shown, this is section "G". In the jacket shown in FIGS. 7 and 8 the sections can be for example:

| Section | Material | | Length |
|---------|----------|---|--------|
| A | polyether/amide | 25 or 35 D durometer | 3-6 cm |
| B | polyether/amide | 40 D durometer | 5-6 cm |
| C | polyether/amide | 55 D durometer | 5-6 cm |
| D | polyether/amide | 63 D durometer | 5-6 cm |
| E | polyether/amide | 72 D durometer | 16 cm |
| F | polyamide/nylon | 0.031 diameter | 10 cm |
| G | polyamide/nylon | 0.034 diameter | To end |

Generally, as shown in FIG. 9 the outer jacket 30 extends past the distal end of wire braid 20 and ends essentially at the distal end of inner liner 10. In some embodiments the inner liner 10 may extend out beyond the distal end of outer jacket 30.

Other Features

A balloon or other occluding member may be attached at or near the distal end of the catheter. Split marker bands 50 and 51 may be used to impart fluoroscopic visibility to the catheter shaft as shown in FIGS. 2 and 9. The more proximal marker band may be disposed over the braid 20 and under the outer jacket 30, whereas the more distal marker band is placed adjacent to the end of the braid 20 over the inner liner 10 and under the outer jacket 30.

EXAMPLES

Example 1

According to one example of the present invention, two catheters were formed of the materials and by the steps described below.

Two different Nitinol braids were cut to 155 cm in length for use in formation of the two catheters. The braids were each formed of eight elliptical 0.001"×0.003" wires. The braids were formed on a steeger braider with the braider pitch changed between segments to form a continuous braid with a changing pitch The first braid had the following segments with the following pics-per-inch (ppi) starting from the distal end: 4 inches 120 ppi, 8 inches 70 ppi, 2 inches 40 ppi, 6 inches 30 ppi, and 39 inches 16 ppi. The second braid had the following segments starting from the distal end: 2 inches 120 ppi, 6 inches 110 ppi, 2 inches 50 ppi, 4 inches 40 ppi, 6 inches 30 ppi, and 39 inches 16 ppi. The remainder of the steps and materials were the same for the two catheters.

A liner of a polyimide layer overlapping a PTFE layer was purchased preloaded on a mandrel. The Nitinol braid placed onto the liner and secured at the ends.

A proximal jacket of Grilamid TR55 (TR55) and Grilamid L25 was then placed on top of the braid. The proximal jacket is described in Table 1. A FEP shrink tube was then placed over the proximal jacket and the proximal portion of the catheter was fused using a pipe line fuser at 450 degrees C. and a speed of 30 cm/min. The FEP was then removed with a mechanical stripper.

TABLE 1

| Distance from Tip (cm) | Distance from Hub (cm) | PPI | Jacket | Estimated Stiffness (.001 in-lbs) | Estimated Kink Resistance ( ) |
|---|---|---|---|---|---|
| 150 | 0 | 16 | TR55 | 13-15 | 90 |
| 50 | 100 | 16 | TR55 | 13-15 | 90 |
| 45-50 | 100-105 | 16-30 | TR55 | 10-15 | 90-130 |
| 45 | 105 | 30 | TR55 | 10 | 120-130 |
| 35 | 115 | 30 | TR55 | 10 | 120-130 |
| 30-35 | 115-120 | 30-40 | TR55 | 8-10 | 120-140 |
| 30 | 120 | 40 | TR55 | 8-9 | 130-140 |
| 25 | 125 | 40 | L25 | 6-7 | 140 |

Three different durometer Pebax distal jackets were then placed on the catheter, as described in Table 2, having durometers of 63D, 35D, and 25D. The segments were tacked in place by fusing with short segments of FEP at the joints. A long piece of FEP shrink tube was placed over all three distal jackets and the distal portion of the catheter was fused using a heat gun at 375 degrees C. The FEP was then removed with a mechanical stripper. The mandrel was removed from the inner lumen of the catheter.

TABLE 2

| Distance from Tip (cm) | Distance from Hub (cm) | PPI | Jacket | Estimated Stiffness (.001 in-lbs) | Estimated Kink Resistance ( ) |
|---|---|---|---|---|---|
| 20-25 | 125-130 | 40-50 | P63D | 5-6 | 140 |
| 5-20 | 130-145 | 50-110 | P35D | 0.5-2 | 140-160 |
| 0-5 | 145-150 | 110-120 | P25D | <0.5 | 160+ |

The complete catheter 5 were tested with a Tinius Olsen stiffness tester.

Example 2

A microcatheter was constructed as follows. A PTFE liner coated along its proximal end with polyimide was obtained. The polyimide coating was tapered between the coated and uncoated regions. The liner had an inside diameter of 0.17 inch (0.43 mm) and was more flexible in its uncoated region than in its coated region. This liner was placed on a suitable mandrel.

A Nitinol braid of the general type set out in Example 1 was obtained. This braid had 5 sections with the following five different pic per inch rates as shown in FIG. 6 and Table 3.

TABLE 3

| | Section | Pic/Inch | Nominal Section Length |
|---|---|---|---|
| Distal | V | 120 | 15 cm. |
| | W | 80 | 15 cm. |
| | X | 50 | 5 cm. |
| | Y | 30 | 15 cm. |
| Proximal | Z | 25 | 100+ cm. |

The braid was placed over the liner with the transition from 25 Pic to 30 Pic weave aligned somewhat distal to the end of the polyamide coating on the PTFE liner.

A polymer jacket was prepared by heat fusing seven cylindrical sections of polymers of varying stiffness to one another. The sections were fused beginning with the stiffest sections which make up the proximal end of the jacket and continuing to the more flexible sections as shown in FIGS. 7 and 8 and Table 4.

TABLE 4

| Section | Material | | | |
|---|---|---|---|---|
| G | Polyamide/nylon | 0.034" | 118 cm | 50" |
| F | Polyamide/nylon | 0.031" | 10 cm | 4" |
| E | Polyether/polyamide | 72 D durometer | 16 cm | 6½" |
| D | Polyether/polyamide | 63 D durometer | 5.5 cm | 2¼" |
| C | Polyether/polyamide | 55 D durometer | 5.5 cm | 2¼" |
| B | Polyether/polyamide | 40 D durometer | 6 cm | 2⅜" |
| A | Polyether/polyamide | 35 D durometer | 3.5 cm | 1⅜" |

The constructed polymer jacket was then assembled over the braid. The jacket was aligned with the distal end of the braid so that the end of the jacket extended slightly beyond the distal end of the braid. A last section of jacket, the most flexible, about 5-6 cm (2-2½") of durometer 35 polyether/polyamide was then lapped slightly over the distal end of section A of the jacket. The distal end of the liner extending beyond the jacket was trimmed to length.

A heat shrink tube was slid over the jacket and the assembled catheter placed in a heat shrink machine and heated in a 260 second cycle to form the jacket tightly around the braid.

Thereafter the shrink tubing was removed and the catheter was mounted onto a hub assembly, the most distal section of flexible liner and jacket was trimmed and the distal end was finished. The trimmed catheter was then given a two step coating with a lubricous, hydrophilic biocompatible coating system known in the art as follows.

The catheter was placed on a coating mandrel and dipped first in a base coat of a polyisocyanate solution with hyaluronic acid polymer and dried and then top-coated with a cross-linked top coat and again dried in a warm oven. This catheter has an outside diameter of 1.9 F (0.63 mm—0.025") at its distal end and 2.4 F (0.79 mm—0.32") at its proximal end.

The lubricous coating covered the catheter from the distal tip and extended back about 100 cm toward the proximal end Example 3

Example 2 was repeated with the following changes:

The wire braid was made of 0.003×0.0007" elliptical wire, jacket section A was 25 durometer polyether/polyamide and the final outside diameter of the finished catheter was 1.7 F (0.57 mm—0.023") at the distal end and 2.1 F (0.70 mm—0.028") at the proximal end.

Example 4

Example 2 was repeated with the following change: A larger diameter PTFE liner was used (0.53 mm—0.21" vs. 0.43 mm—0.17"). The materials for the braid and jacket were as described in Example 2. The resulting catheter had a distal diameter of 2.2 F (0.73 mm—0.029") and a proximal diameter of 2.7 F (0.9 mm—0.036").

Example 5

The microcatheter of Example 2 was tested to determine kink resistance using standard methods and procedures known in the art. The results are presented in the Table 5 below.

TABLE 5

| Kink Resistance | |
|---|---|
| Location on Catheter | Diameter of Kink (inches) |
| Distal Tip | 0.035 |
| Distal Shaft (3-22 cm) | 0.038-0.081 |
| Middle Shaft (22-44 cm) | 0.101-0.113 |
| Proximal Shaft (44 cm-65 cm) | 0.116-0.107 |

The microcatheter of Example 2 was also tested to determine burst strength using standard methods and procedures known in the art. The results are presented in Table 6 below.

TABLE 6

| Static Burst Pressure | |
|---|---|
| Location on Catheter (Distance from the Distal Tip (cm)) | Burst Pressure (psi) |
| 3.2 | 969 |
| 3.5 | 820 |
| 8 | 846 |
| 22.2 | 840 |
| 24.1 | 977 |
| 27.5 | 868 |
| 29.2 | 774 |
| 38 | 716 |
| 42 | 688 |
| 45 | 900 |

According to the above data, the catheter has an average burst pressure of 837 psi.

Example 6

The microcatheter of Example 3 was tested to determine kink resistance using standard methods and procedures known in the art. The results of the test are presented in the Table 7 below.

TABLE 7

| Kink Resistance | |
|---|---|
| Location on Catheter | Diameter of Kink (inches) |
| Distal Tip | 0.014 |
| Distal Shaft (3-22 cm) | 0.025 |
| Middle Shaft (22-44 cm) | 0.056 |
| Proximal Shaft (44 cm-65 cm) | 0.150 |

The microcatheter of Example 3 was also tested for burst pressure and was found to have an average burst pressure of 742 psi.

While the invention has been described in detail with reference to the preferred embodiments thereof, it will be apparent to one skilled in the art that various changes and modifications can be made and equivalents employed, without departing from the present invention.

What is claimed is:

1. A braid-reinforced microcatheter having a degree of flexibility to traverse remote vascular locations and a degree of strength to withstand high pressure associated with catheter delivery of viscous liquid embolizing compositions comprising:
   a) a cylindrical inner layer of polymer defining a single lumen in the catheter wherein said inner layer has a proximal end and a distal end and a flexibility at its distal end greater than at its proximal end further wherein said inner layer consists essentially of a first or inner polymer layer and a second or outer polymer layer at the proximal end and said first polymer layer at the distal end and still further wherein said first polymer layer is a lubricous polymer selected from the group consisting of polytetrafluoroethylene and high density polyethylene and said second layer comprises polyimide and wherein the second layer gradually tapers to zero at the distal end wherein at least 3-5 cm of the distal end is provided with no polyimide;
   b) a braided wire layer over the inner layer, the braided wire layer including a distal segment of a first pic rate and a proximal segment of a second pic rate which is smaller than the first pic rate, the braided wire layer extending from the proximal end to within about 1 cm of the distal end of the catheter;
   c) an outer jacket surrounding the braided wire comprising a plurality of joined segments of polymers of increasing flexibility thereby having a proximal durometer higher than a distal durometer; and
   d) wherein the microcatheter is devoid of a balloon and wherein the microcatheter has a burst strength of from 700 to 1000 psi.

2. The microcatheter of claim 1 wherein the wire braid comprises Nitinol.

3. The microcatheter of claim 1 wherein the wire braid comprises stainless steel.

4. The microcatheter of claim 1 wherein the wire braid consists essentially of Nitinol.

5. The microcatheter of claim 1 or 2 or 4 wherein the wire braid contains about 8 wires.

6. The microcatheter of claim 1 or 2 or 4 wherein the wire in the braid is elliptical in cross section.

7. The microcatheter of claim 1 or 2 or 4 wherein the pic rate of the wire braid in its least flexible portion is less than ¼ the pic rate of its most flexible portion.

8. The microcatheter of claim 1 wherein the pic rate of the wire braid changes continuously.

9. The microcatheter of claim 1 wherein the pic rate of the wire braid changes stepwise.

10. The microcatheter of claim 9 wherein the pic rate changes in at least 3 steps.

11. The microcatheter of claim 9 wherein the pic rate changes in 4 steps.

12. The microcatheter of claim 1 wherein the polymer jacket comprises polyamide/nylon at its proximal end.

13. The microcatheter of claim 1 wherein the polymer jacket comprises polyether-polyamide block copolymer at its distal end.

14. The microcatheter of claim 1 wherein the polymer jacket comprises at least one segment of polyamide/nylon and at least two segments of polyether-polyamide block copolymer.

15. The microcatheter of claim 1 wherein the most flexible segments of the polymer jacket have a durometer of about 35 or less.

16. The microcatheter of claim 1 wherein the most flexible segments of the polymer jacket have a durometer of about 35.

17. The microcatheter of claim 1 wherein the most flexible segments of the polymer jacket have a durometer of about 25.

18. The microcatheter of claim 1 comprising:
   a) a cylindrical inner layer of polymer defining a single lumen in the catheter wherein said inner layer has a proximal end and a distal end and a flexibility at its distal end greater than at its proximal end further wherein said inner layer consists essentially of a first or inner polymer layer and a second or outer polymer layer at the proximal end and said first polymer layer at the distal end and still further wherein said first polymer layer is a lubricous polymer selected from the group consisting of polytetrafluoroethylene and high density polyethylene and said second layer comprises polyimide and wherein the second layer gradually tapers to zero at the distal end wherein at least 3-5 cm of the distal end is provided with no polyimide;
   b) a braided wire layer over the inner layer, the braided wire layer including a distal segment of a first pic rate and a proximal segment of a second pic rate which is smaller than the first pic rate, the braided wire layer extending from the proximal end to within about 1 cm of the distal end of the catheter wherein the braided wire layer comprises five sections with five different pic per inch rates as shown in Table 3 below;

TABLE 3

|  | Section | Pic/Inch | Nominal section length |
|---|---|---|---|
| Distal | V | 120 | 15 cm |
|  | W | 80 | 15 cm |
|  | X | 50 | 5 cm |
|  | Y | 30 | 15 cm |
| Proximal | Z | 25 | 100 + cm | c) an outer jacket surrounding the braided wire comprising a seven cylindrical sections of joined segments of polymers of increasing flexibility thereby having a proximal durometer higher than a distal durometer as shown in Table 4 below;

TABLE 4

| Section | Material | | | |
|---|---|---|---|---|
| G | Polyamide/nylon | 0.034" | 118 cm | 50" |
| F | Polyamide/nylon | 0.031" | 10 cm | 4" |
| E | Polyether/polyamide | 72 D durometer | 16 cm | 6½" |
| D | Polyether/polyamide | 63 D durometer | 5.5 cm | 2¼" |
| C | Polyether/polyamide | 55 D durometer | 5.5 cm | 2¼" |
| B | Polyether/polyamide | 40 D durometer | 6 cm | 2⅜" |
| A | Polyether/polyamide | 35 D durometer | 3.5 cm | 1⅜" | and
   d) wherein the microcatheter is devoid of a balloon and wherein said microcatheter has a burst strength of from 700 to 1000 psi.

* * * * *

UNITED STATES PATENT AND TRADEMARK OFFICE
CERTIFICATE OF CORRECTION

| | |
|---|---|
| PATENT NO. | : 7,507,229 B2 |
| APPLICATION NO. | : 10/683877 |
| DATED | : March 24, 2009 |
| INVENTOR(S) | : Hewitt et al. |

It is certified that error appears in the above-identified patent and that said Letters Patent is hereby corrected as shown below:

On the Title Page,

Item [*] Notice: Subject to any disclaimer, the term of this patent is extended or adjusted under 35 USC 154(b) by 255 days Delete the phrase "by 255 days" and insert -- by 487 days --

Signed and Sealed this

Eleventh Day of May, 2010

David J. Kappos
*Director of the United States Patent and Trademark Office*